United States Patent
Ottoboni et al.

(10) Patent No.: US 12,290,520 B2
(45) Date of Patent: *May 6, 2025

(54) METHODS OF USE OF EMULSION FORMULATIONS OF APREPITANT

(71) Applicant: Heron Therapeutics, Inc., San Diego, CA (US)

(72) Inventors: Thomas B. Ottoboni, Belmont, CA (US); Han Han, Mountain View, CA (US)

(73) Assignee: Heron Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/408,463

(22) Filed: Jan. 9, 2024

(65) Prior Publication Data

US 2024/0139201 A1    May 2, 2024

Related U.S. Application Data

(63) Continuation of application No. 17/194,114, filed on Mar. 5, 2021, now abandoned, which is a
(Continued)

(51) Int. Cl.
*A61K 9/10* (2006.01)
*A61K 9/00* (2006.01)
(Continued)

(52) U.S. Cl.
CPC ........ *A61K 31/5377* (2013.01); *A61K 9/0019* (2013.01); *A61K 9/0024* (2013.01);
(Continued)

(58) Field of Classification Search
CPC .............. A61K 31/5377; A61K 9/0019; A61K 9/0024; A61K 9/107; A61K 31/573;
(Continued)

(56) References Cited

U.S. PATENT DOCUMENTS

| 1,062,485 A | * 5/1913 | Ottoboni ................ B65G 67/00 193/42 |
| 5,616,330 A | 4/1997 | Kaufman et al. |

(Continued)

FOREIGN PATENT DOCUMENTS

| CN | 102379845 A | * 3/2012 |
| CN | 103520725 A | 1/2014 |

(Continued)

OTHER PUBLICATIONS

Weng et al. (Eur. J. Lipid. Sci. Technol. 2012;114:1154-1164) (Year: 2012).*

(Continued)

*Primary Examiner* — Ernst V Arnold
(74) *Attorney, Agent, or Firm* — McDermott Will & Emery LLP; Judy M. Mohr; Brennen P. Baylor (57) ABSTRACT

Disclosed herein are novel pharmaceutical formulations of aprepitant suitable for parenteral administration including intravenous administration. Also included are formulations including both aprepitant and dexamethasone sodium phosphate. The pharmaceutical formulations are stable oil-in-water emulsions for non-oral treatment of emesis and are particularly useful for treatment of subjects undergoing highly emetogenic cancer chemotherapy.

24 Claims, 4 Drawing Sheets

Related U.S. Application Data continuation of application No. 16/669,262, filed on Oct. 30, 2019, now Pat. No. 10,953,018, which is a continuation of application No. 15/398,928, filed on Jan. 5, 2017, now Pat. No. 10,500,208, which is a continuation of application No. 15/083,071, filed on Mar. 28, 2016, now Pat. No. 9,561,229, which is a continuation of application No. 14/859,013, filed on Sep. 18, 2015, now Pat. No. 9,808,465.

(60) Provisional application No. 62/052,948, filed on Sep. 19, 2014.

(51) Int. Cl.
| | |
|---|---|
| *A61K 9/107* | (2006.01) |
| *A61K 31/00* | (2006.01) |
| *A61K 31/5377* | (2006.01) |
| *A61K 31/573* | (2006.01) |
| *A61K 47/10* | (2017.01) |
| *A61K 47/12* | (2006.01) |
| *A61K 47/18* | (2017.01) |
| *A61K 47/24* | (2006.01) |
| *A61K 47/26* | (2006.01) |
| *A61K 47/44* | (2017.01) |

(52) U.S. Cl.
CPC ............ *A61K 9/107* (2013.01); *A61K 31/573* (2013.01); *A61K 47/10* (2013.01); *A61K 47/12* (2013.01); *A61K 47/18* (2013.01); *A61K 47/24* (2013.01); *A61K 47/26* (2013.01); *A61K 47/44* (2013.01)

(58) Field of Classification Search
CPC ........ A61K 47/10; A61K 47/12; A61K 47/18; A61K 47/24; A61K 47/26; A61K 47/44
See application file for complete search history.

(56) References Cited

U.S. PATENT DOCUMENTS

| | | | |
|---|---|---|---|
| 9,561,229 B2* | 2/2017 | Ottoboni | A61K 47/24 |
| 9,808,465 B2* | 11/2017 | Ottoboni | A61K 47/12 |
| 9,974,742 B2* | 5/2018 | Ottoboni | A61K 9/1075 |
| 9,974,793 B2* | 5/2018 | Ottoboni | A61K 47/24 |
| 9,974,794 B2* | 5/2018 | Ottoboni | A61K 9/0024 |
| 10,500,208 B2* | 12/2019 | Ottoboni | A61P 43/00 |
| 10,624,850 B2 | 4/2020 | Ottoboni et al. | |
| 10,953,018 B2* | 3/2021 | Ottoboni | A61K 47/44 |
| 11,173,118 B2* | 11/2021 | Ottoboni | A61K 31/43 |
| 11,744,800 B2* | 9/2023 | Ottoboni | A61K 31/573 707/750 |
| 11,878,074 B2* | 1/2024 | Ottoboni | A61K 31/435 |
| 2007/0071777 A1 | 3/2007 | Bromer et al. | |
| 2011/0009362 A1 | 1/2011 | Joshi et al. | |
| 2011/0038925 A1 | 2/2011 | Wan | |
| 2012/0045489 A1* | 2/2012 | Tong | A61K 9/0019 977/773 |
| 2013/0236501 A1 | 9/2013 | Booth et al. | |
| 2013/0317016 A1 | 11/2013 | Hingorani et al. | |
| 2016/0024092 A1 | 1/2016 | Wan et al. | |
| 2016/0082013 A1 | 3/2016 | Ottoboni et al. | |
| 2016/0206622 A1 | 3/2016 | Ottoboni et al. | |
| 2017/0112847 A1 | 4/2017 | Ottoboni et al. | |
| 2017/0216205 A1 | 8/2017 | Ottoboni et al. | |
| 2018/0000828 A1 | 1/2018 | Ottoboni et al. | |
| 2018/0000829 A1 | 1/2018 | Ottoboni et al. | |
| 2019/0000762 A1 | 1/2019 | Ottoboni et al. | |
| 2020/0383914 A1 | 12/2020 | Ottoboni et al. | |
| 2021/0173877 A1 | 6/2021 | Ottoboni et al. | |
| 2023/0072781 A1 | 3/2023 | Ottoboni et al. | |

FOREIGN PATENT DOCUMENTS

| | | |
|---|---|---|
| JP | 01-113315 A | 5/1989 |
| JP | 2005-225818 A | 8/2005 |
| WO | WO 2005/016308 A1 | 2/2005 |
| WO | WO 2009/124756 A1 | 10/2009 |
| WO | WO 2011/158053 A1 | 12/2011 |
| WO | WO 2013/101749 A1 | 7/2013 |
| WO | WO 2013/177501 A2 | 11/2013 |
| WO | WO 2014/005606 A1 | 1/2014 |
| WO | WO 2014/209962 A1 | 12/2014 |
| WO | WO 2016/044784 A1 | 3/2016 |
| WO | WO 2017/135923 | 8/2017 |

OTHER PUBLICATIONS

Applicant initiated interview, Examiners Summary, Aug. 31, 2016, for U.S. Appl. No. 15/083,071, now U.S. Pat. No. 9,561,229, 4 pages (2016).
Aziz, "Neurokinin-1 receptor antagonists for chemotherapy-induced nausea and vomiting", Ann. Palliat. Med., vol. 1, No. 2, pp. 130-136 (2012).
Dando and Perry, "Aprepitant: a review of its use in the prevention of chemotherapy-induced nausea and vomiting", Drugs, vol. 64, No. 7, pp. 777-794 (2004).
Declaration of Thomas Ottoboni under 37 C.F.R. § 1.132, filed Sep. 1, 2016 in regard to U.S. Appl. No. 15/083,071, now U.S. Pat. No. 9,561,229, 9 pages (2016).
Dexamethasone Sodium Phosphate retrieved from the internet from web.archive.org/web/20141224130045/http://www.drugs.com/pro/dexamethasone-sodium-phosphate.html (2017).
Cassileth et al., "Antiemetic efficacy of dexamethasone therapy in patients receiving cancer chemotherapy", Arch. Intern. Med., vol. 143, No. 7, pp. 1347-1349 (1983) Abstract Only.
Curran et al., "Aprepitant: a review of its use in the prevention of nausea and vomiting", Drugs, vol. 69, No. 13, pp. 1853-1878 (2009).
Hargreaves et al., "Development of aprepitant, the first neurokinin-1 receptor antagonist for the prevention of chemotherapy-induced nausea and vomiting", Ann. N.Y. Acad. Sci., vol. 1222, pp. 40-48 (2011).
International Search Report from PCT Patent Application No. PCT/US2015/051050 mailed Dec. 18, 2015, Application now published as International Publication No. WO2016/044784 on Mar. 24, 2016.
International Search Report from PCT Patent Application No. PCT/2016/015992 mailed Jun. 3, 2016, Application now published as International Publication No. WO2017/135923 on Aug. 10, 2017.
Lipoid GmbH, Lipoid Product Finder, Retrieved from the internet http://www.lipiod.com/en/node/105, 1 page (2018).
Lipoid GmbH, Lipoid Product Finder, print friendly version, Retrieved from the internet <URL: http://www.lipoid.com/en/print/105, 2 pages (2018).
Navari et al., "Reduction of cisplatin-induced emesis by a selective neurokinin-1-receptor antagonist. L-754,030 Antiemetic Trials Group", N. Engl. J. Med., vol. 340, No. 3, pp. 190-195 (1999).
Sun et al., "Compatibility of intravenous fosaprepitant with intravenous 5-HT3 antagonists and corticosteroids", Cancer Chemother. Pharmacol., vol. 72, No. 3, pp. 509-513 (2013).
Takagi, "New emulsification technology searching for a harmonization of formulation and mechanical emulsification method", Fragrance J., No. 19, pp. 131-138 (2005) English Abstract.
Takahashi et al., "Pharmacokinetics of aprepitant and dexamethasone after administration of chemotherapeutic agents and effects of plasma substance P concentration on chemotherapy-induced nausea and vomiting in Japanese cancer patients", Cancer Cheother. Pharmacol., vol. 68, No. 3, pp. 653-659 (2011).
The Pharmaceutics and Compounding Laboratory, "Emulsions: Preparation and Stabilization, Methods of emulsion preparation", 1 page, Online article accessed May 26, 2016 from http://pharmlabs.unc.edu/labs/emulsions/prep.htm.

(56) References Cited

OTHER PUBLICATIONS

Weng et al., "Formulation, preparation, and stability of intravenous bufadienolides-loaded lipid microspheres", Eur. J. Lipid Sci., vol. 114, pp. 1154-1164 (2012).

Zhou et al., "Preparation of Aprepitant emulsion for intravenous injection", Chinese Journal of Pharmaceuticals, vol. 43, No. 12, pp. 1003-1006 (2012) English Translation Only.

* cited by examiner

METHODS OF USE OF EMULSION FORMULATIONS OF APREPITANT

CROSS-REFERENCE TO RELATED APPLICATIONS

This application is a continuation of U.S. application Ser. No. 17/194,114, filed Mar. 5, 2021, which is a continuation of U.S. application Ser. No. 16/669,262, filed Oct. 30, 2019, now U.S. Pat. No. 10,953,018, which is a continuation of U.S. application Ser. No. 15/398,928, filed Jan. 5, 2017, now U.S. Pat. No. 10,500,208, which is a continuation of U.S. application Ser. No. 15/083,071, filed Mar. 28, 2016, now U.S. Pat. No. 9,561,229, issued Feb. 7, 2017, which is a continuation of U.S. application Ser. No. 14/859,013, filed Sep. 18, 2015, now U.S. Pat. No. 9,808,465, issued Nov. 7, 2017, which claims the benefit of U.S. Provisional Application No. 62/052,948 filed on Sep. 19, 2014, the disclosures of which are fully incorporated by reference in their entirety.

TECHNICAL FIELD

The disclosure relates generally to emulsion formulations and systems for the intravenous or parenteral administration of aprepitant for treatment of emesis. The emulsion formulations are stable for prolonged periods of time. Also described are methods for preparing the stable aprepitant emulsions and pharmaceutical formulations.

BACKGROUND

Aprepitant, having the chemical name 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one, has the structure:

Aprepitant is indicated for the prevention of acute and delayed nausea and vomiting associated with initial and repeat courses of highly emetogenic cancer chemotherapy. Aprepitant is currently available in the United States as an oral capsule, however due to the nausea and vomiting experienced by patients, it is desirable to formulate aprepitant as a liquid suitable for parenteral or intravenous administration.

Liquid formulations containing aprepitant are very challenging to make as aprepitant is a molecule having poor solubility and poor permeability characteristics. One means of addressing this challenge is to prepare an emulsion which may both allow preparation of an injectable formulation as well as enhance bioavailability of the aprepitant once administered.

Intravenous emulsions should have a very small droplet size to circulate in the bloodstream without causing capillary blockage and embolization. These size limits are typified by USP33-NF28 General Chapter <729> for Globule Size Distribution in Lipid Injectable Emulsions, hereinafter referred to as USP <729>, which defines universal limits for (1) mean droplet size not exceeding 500 nm or 0.5 µm and (2) the population of large-diameter fat globules, expressed as the volume-weighted percentage of fat greater than 5 µm (PFAT5) not exceeding 0.05%, irrespective of the final lipid concentration.

Emulsion formulations must be physically stable. The droplet size limits defined in USP <729> apply throughout the assigned shelf life. All true emulsions are thermodynamically unstable and may over time undergo a range of processes which tend to increase the droplet size. These include direct droplet coalescence, when two droplets collide and form a single new droplet, and aggregation, in which droplets adhere together to form larger masses. Aggregation may in some cases be a precursor of further coalescence into larger droplets. These processes may result in large aggregates rising to the surface of the container, a phenomenon known as 'creaming', and ultimately to free oil being visible on the emulsion surface, known as 'cracking'.

Emulsion formulations must also be chemically stable. The drug substance may degrade; for example, lipophilic drugs will partition into the oil phase, which will confer some degree of protection, but hydrolytic degradation may still occur at the oil-water interface. Possible chemical degradation within parenteral fat emulsions includes oxidation of unsaturated fatty acid residues present in triglyceride and lecithin, and hydrolysis of phospholipids leading to the formation of free fatty acids (FFA) and lysophospholipids. Such degradants lower pH, which may then promote further degradation. Thus, pH should be controlled during manufacture and parenteral emulsion formulations may include a buffering agent to provide additional control. Any decrease in pH over the assigned shelf-life may be indicative of chemical degradation.

In the present application, emulsion formulations were prepared and characterized to identify a formulation and process that will allow aprepitant to be incorporated into an emulsion for intravenous injection and remain stable during the shelf life of the formulation.

BRIEF SUMMARY

The following aspects and embodiments thereof described and illustrated below are meant to be exemplary and illustrative, not limiting in scope.

In one aspect, a pharmaceutical composition suitable for intravenous administration is provided which comprises a stable emulsion comprising an oil phase, wherein the oil phase comprises aprepitant, a surfactant and a co-surfactant; and an aqueous phase, wherein the aqueous phase comprises water, a tonicity agent and a pH-adjusting agent. In some embodiments, the pH-adjusting agent is a buffer.

In one embodiment, the composition is an oil-in-water emulsion comprising an oil selected from the group consisting of structurally modified or hydrolyzed coconut oil, olive oil, soybean oil, safflower oil, triglycerides, octyl and decyl glycerate, ethyl oleate, glyceryl linoleate, ethyl linoleate, glyceryl oleate, cholesteryl oleate/linoleate or a mixture thereof.

In one embodiment, the composition comprises about 5 wt/wt % (weight/weight %) to 15 wt/wt %, 5 wt/wt % to 10 wt/wt %, 7 wt/wt % to 10 wt/wt % or 8 wt/wt % to 9 wt/wt % oil. In another embodiment, the oil is soybean oil.

In one embodiment, the composition comprises about 10 wt/wt % to 20 wt/wt %, 12 wt/wt % to 17 wt/wt %, 13 wt/wt % to 16 wt/wt %, 13 wt/wt % to 15 wt/wt %, or 13 wt/wt % to 14 wt/wt % emulsifier. In another embodiment, the composition comprises about 13 wt/wt %, 13.5 wt/wt %, 14 wt/wt %, 14.5 wt/wt %, 15 wt/wt %, 16 wt/wt %, 17 wt/wt %, 18 wt/wt %, 19 wt/wt % or 20 wt/wt % emulsifier. In another embodiment the emulsifier is a lecithin. In another embodiment the lecithin is an egg yolk lecithin.

In one embodiment, the composition comprises about 20 wt/wt % to 50 wt/wt %, 30 wt/wt % to 50 wt/wt %, 35 wt/wt % to 45 wt/wt %, 30 wt/wt % to 45 wt/wt %, 37 wt/wt % to 42 wt/wt %, 38 wt/wt % to 40 wt/wt %, 30 wt/wt %, 31 wt/wt %, 32 wt/wt %, 33 wt/wt %, 34 wt/wt %, 35 wt/wt %, 36 wt/wt %, 37 wt/wt %, 38 wt/wt %, 39 wt/wt %, 40 wt/wt %, 41 wt/wt %, 42 wt/wt %, 43 wt/wt %, 44 wt/wt %, 45 wt/wt %, 46 wt/wt %, 47 wt/wt %, 48 wt/wt %, 49 wt/wt %, 50 wt/wt % of oil expressed as a percentage of the weight of the oil per the sum of weight of oil, emulsifier and oleate in a unit of the composition. In another embodiment, the oil is soybean oil.

In one embodiment, the composition comprises about 40 wt/wt % to 80 wt/wt %, 50 wt/wt % to 70 wt/wt %, 55 wt/wt % to 65 wt/wt %, 57 wt/wt % to 63 wt/wt %, 58 to 60 wt/wt %, 35 wt/wt % to 40 wt/wt %, 30 wt/wt % to 40 wt/wt %, 50 wt/wt %, 51 wt/wt %, 52 wt/wt %, 53 wt/wt %, 54 wt/wt %, 55 wt/wt %, 56 wt/wt %, 57 wt/wt %, 58 wt/wt %, 59 wt/wt %, 60 wt/wt %, 61 wt/wt %, 62 wt/wt %, 63 wt/wt %, 64 wt/wt %, 65 wt/wt %, 66 wt/wt %, 67 wt/wt %, 68 wt/wt %, 69 wt/wt %, 70 wt/wt % of emulsifier expressed as a percentage of the weight of emulsifier per the sum of weight of oil, emulsifier and oleate in a unit of the composition. In another embodiment the emulsifier is a lecithin. In another embodiment the lecithin is an egg yolk lecithin.

In one embodiment, the ratio of oil to aprepitant (wt %:wt %) in the composition ranges from about 11:1 to 20:1, 11:1 to 15:1, 12:1 to 16:1, 12:1 to 14:1, 11:1 to 15:1, 12:1 to 14:1, 12.5:1 to 13.5:1, 13:1 to 14:1, or 12:1 to 15:1. In another embodiment, the ratio of oil to aprepitant (wt %:wt %) in the composition is about 11:1 to 20:1, 11:1 to 15:1, 12:1 to 16:1, 12:1 to 14:1, 11:1, 11.5:1, 12:1, 12.5:1, 13:1, 13.5:1, 14:1, 14.5:1 or 15:1, 15.5:1, 16:1.

In one embodiment, the ratio of emulsifier to aprepitant (wt %:wt %) in the composition ranges from about 15:1 to 30:1, 20:1 to 25:1, 18:1 to 22:1 or 10:1 to 30:1. In another embodiment, the ratio of emulsifier:aprepitant (wt %:wt %) in the composition is about 15:1, 18:1, 19:1, 20:1, 21:1, 22:1 23:1, 24:1, or 25:1.

In one embodiment, the ratio of (emulsifier plus oil) to aprepitant (wt %:wt %) in the composition ranges from about 20:1 to 40:1, 25:1 to 35:1, 30:1 to 35:1. In another embodiment, the ratio of oil:aprepitant is about 25:1, 26:1, 27:1, 28:1, 29:1 30:1, 31:1, 32:1, 33:1, 34:1, 35:1, 36:1, 37:1, 38:1 or 40:1.

In one embodiment, the ratio of emulsifier to oil (wt %:wt %) in the composition ranges from about 0.5:1 to 4:1, 1:1 to 2:1, or 1.25:1 to 1.75:1. In another embodiment, the ratio of emulsifier to oil (wt %:wt %) in the composition is about 0.5:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 1.05:1, 1.15:1, 1.25:1, 1.35:1, 1.45:1, 1.55:1, 1.65:1, 1.75:1, 1.85:1, or 1.95:1.

In one embodiment, a therapeutic dose comprises about 1 to 4 g, 1.5 to 3 g, 1.8 to 2.8 g, 2.3 to 2.8 g, 1.8 to 2.3 g, 1 g, 1.1 g, 1.2 g, 1.3 g, 1.4 g, 1.5 g, 1.6 g, 1.7 g, 1.8 g. 1.9 g, 2 g, 2.1 g, 2.2 g, 2.3 g, 2.4 g, 2.5 g, 2.6 g, 2.7 g, 2.8 g. 2.9 g, 3 g, 3.1 g, 3.2 g, 3.3 g, 3.4 g, 3.5 g, 3.6 g, 3.7 g, 3.8 g, 3.9 g, 4 g emulsifier. In another embodiment, the emulsifier is a lecithin. In another embodiment the emulsifier is egg yolk lecithin.

In one embodiment, a therapeutic dose comprises about 0.5 to 3 g, 1 to 2.5 g, 1 to 2 g, 1 to 1.5 g, 1.5 g to 2 g, 0.5 g 0.6 g, 0.7 g, 0.8 g, 0.9 g, 1 g, 1.1 g, 1.2 g, 1.3 g, 1.4 g, 1.5 g, 1.6 g, 1.7 g, 1.8 g. 1.9 g, 2 g, 2.1 g, 2.2 g, 2.3 g, 2.4 g, 2.5 g oil. In another embodiment, the oil is soybean oil.

In one embodiment, the emulsifier is a phospholipid. In another embodiment, the emulsifier is selected from the group consisting of egg phospholipids, soy phospholipids, phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

In one embodiment, the composition comprises a co-surfactant. In another embodiment, the co-surfactant is ethanol.

In one embodiment, the composition comprises about 0 wt/wt % to 10 wt/wt %, 1 wt/wt % to 9 wt/wt %, or 2 wt/wt % to 6 wt/wt % co-surfactant. In another embodiment, the composition comprises less than 10 wt/wt %, less than 9 wt/wt %, less than 8 wt/wt %, less than 7, less than 6 wt/wt %, less than 5 wt/wt %, less than 4 wt/wt %, less than 3 wt/wt %, less than 2 wt/wt % or less than 1 wt/wt % co-surfactant.

In one embodiment, the composition comprises about 0 wt/wt % to 10 wt/wt %, 1 wt/wt % to 9 wt/wt %, or 2 wt/wt % to 6 wt/wt % ethanol. In another embodiment, the composition comprises less than 10 wt/wt %, less than 9 wt/wt %, less than 8 wt/wt %, less than 7, less than 6 wt/wt %, less than 5 wt/wt %, less than 4 wt/wt %, less than 3 wt/wt %, less than 2 wt/wt % or less than 1 wt/wt % ethanol.

In one embodiment, the emulsion comprises an aqueous phase which comprises a tonicity agent, a pH-adjusting agent, and water.

In one embodiment, the emulsion comprises an aqueous phase which comprises an osmotic agent, a pH-adjusting agent, and water.

In one embodiment, the emulsion comprises an aqueous phase which comprises a tonicity agent, an osmotic agent, a pH-adjusting agent, and water.

In one embodiment, the aqueous phase further comprises a buffer.

In one embodiment, the aqueous phase comprises a buffer but does not comprise a pH-adjusting agent which is different than the buffer. In another embodiment, the buffer functions as both a pH-adjusting agent and a buffer.

In another embodiment, when the aqueous phase comprises a buffer, the composition contains no tonicity agent.

In one another embodiment, the buffer is selected from the group consisting of phosphate buffer, citrate buffer, Tris buffer, carbonate buffer, succinate buffer, maleate buffer and borate buffer. In another embodiment, the buffer is selected from the group, phosphate buffered saline (PBS), modified PBS (PBS-mod) and citrate buffer.

In one embodiment, the aqueous phase comprises a buffer, that when mixed with the oil phase will provide a substantially isotonic oil in water emulsion.

In one embodiment, the osmotic agent is selected from the group consisting of glycerol, sorbitol, xylitol, mannitol, glucose, trehalose, maltose, sucrose, raffinose, lactose, dextran, polyethylene glycol, or propylene glycol. In another embodiment, the osmotic agent is an inorganic salt such as sodium chloride and mixtures thereof.

In one embodiment, the pH adjusting agent is selected from the group consisting of sodium hydroxide, potassium hydroxide, magnesium hydroxide, sodium carbonate, Tris, sodium linoleate, sodium oleate, potassium carbonate, potassium linoleate, potassium oleate, and mixtures thereof.

In one embodiment, the composition has a pH of about 6 to 9, 7 to 9, 7.5 to 9, 7.5 to 8.5, 8 to 9, 6 to 8, 7 to 8, or 6, 7, 8 or 9.

In one embodiment, the composition comprises about 0 wt/wt % to 25 wt/wt %, 2 wt/wt % to 20 wt/wt %, 3 wt/wt % to 15 wt/wt %, or 3 wt/wt % to 8 wt/wt % tonicity agent. In another embodiment, the composition comprises about 1 wt/wt %, 2 wt/wt %, 3 wt/wt %, 4 wt/wt %, 5 wt/wt %, 6 wt/wt %, 7 wt/wt %, 8 wt/wt %, 9 wt/wt %, or 10 wt/wt %, 11 wt/wt %, 12 wt/wt %, 13 wt/wt %, 14 wt/wt %, 15 wt/wt %, 16 wt/wt %, 17 wt/wt %, 18 wt/wt %, 19 wt/wt %, or 20 wt/wt %, 21 wt/wt %, 22 wt/wt %, 23 wt/wt %, 24 wt/wt %, 25 wt/wt % tonicity agent. In still another embodiment, the composition comprises no tonicity agent.

In one embodiment, the composition comprises about 0 wt/wt % to 25 wt/wt %, 2 wt/wt % to 20 wt/wt %, 3 wt/wt % to 15 wt/wt %, or 3 wt/wt % to 8 wt/wt % osmotic agent. In another embodiment, the composition comprises about 1 wt/wt %, 2 wt/wt %, 3 wt/wt %, 4 wt/wt %, 5 wt/wt %, 6 wt/wt %, 7 wt/wt %, 8 wt/wt %, 9 wt/wt %, or 10 wt/wt %, 11 wt/wt %, 12 wt/wt %, 13 wt/wt %, 14 wt/wt %, 15 wt/wt %, 16 wt/wt %, 17 wt/wt %, 18 wt/wt %, 19 wt/wt %, or 20 wt/wt %, 21 wt/wt %, 22 wt/wt %, 23 wt/wt %, 24 wt/wt %, 25 wt/wt % osmotic agent. In still another embodiment, the composition comprises no osmotic agent.

In one embodiment, the aqueous phase comprises a dose of dexamethasone sodium phosphate in a dose of the composition. In another embodiment, the dose of dexamethasone sodium phosphate ranges from about 0.5 mg to 30 mg, 0.5 mg to 25 mg, 1 mg to 20 mg, 10 mg to 20 mg, or 3 mg to 16 mg. In another embodiment, the dose of dexamethasone sodium phosphate is about 9 mg or 16 mg in a dose of the composition.

In one embodiment, the oil phase comprises a dose of dexamethasone in a dose of the composition. In another embodiment, the dose of dexamethasone ranges from about 0.5 mg to 30 mg, 0.5 mg to 20 mg, 1 mg to 18 mg, 10 mg to 20 mg, or 3 mg to 16 mg. In another embodiment, the dose of dexamethasone is about 8 mg or 12 mg in a dose of the composition.

In one embodiment, the emulsion comprises about 0.002 wt/wt % to 0.2 wt/wt %, 0.003 wt/wt % to 0.16 wt/wt %, 0.02 wt/wt % to 0.1 wt/wt % dexamethasone sodium phosphate.

In one embodiment, the composition is a stable system maintaining an intensity-weighted mean particle size as determined by dynamic light scattering (DLS) of about 50 nm to 1000 nm, 50 to 500 nm, 50 nm to 400 nm, 50 nm to 300 nm, 50 nm to 200 nm or 50 nm to 100 nm. In another embodiment, the average droplet size is maintained above 500 nm for a period of at least 1 month, 3 months, 6 months, 9 months, 12 months, 2 years or 3 years at room temperature. In another embodiment, the average droplet size is maintained above 500 nm for a period of at least 1 month, 3 months, 6 months, 9 months, 12 months, 2 years or 3 years at 5° C.

In another aspect, a method for preparing an emulsion comprising aprepitant and suitable for parenteral administration is provided.

In one embodiment, the administration is intravenous administration.

In one embodiment, the method comprises: a) preparing an oil phase by dissolving aprepitant and an emulsifier in ethanol, then adding in oil to generate an oil-based mixture; b) preparing an aqueous phase by mixing water, optionally with a tonicity agent, optionally with an osmotic agent and optionally with a pH modifier and optionally with a buffer to generate an aqueous mixture; c) combining the oil-based mixture and the aqueous mixture and subjecting this to high speed homogenization to generate a crude emulsion; and d) subjecting the crude emulsion to high pressure homogenization to generate a fine emulsion.

In one embodiment, preparing the oil phase further comprises dissolving dexamethasone with the aprepitant and the emulsifier in the ethanol.

In one embodiment, the method comprises: a) preparing an oil phase by dissolving aprepitant and an emulsifier in ethanol and oil to generate an oil-based mixture; b) preparing an aqueous phase by mixing water, optionally with a tonicity agent, optionally with an osmotic agent and optionally with a pH modifier and optionally with a buffer to generate an aqueous mixture; c) combining the oil-based mixture and the aqueous mixture and subjecting this to high speed homogenization to generate a crude emulsion; and d) subjecting the crude emulsion to high pressure homogenization to generate a fine emulsion.

In one embodiment, preparing the oil phase further comprises dissolving dexamethasone with the aprepitant and the emulsifier in the ethanol and oil.

In one embodiment, preparing the aqueous phase further comprises mixing dexamethasone with the water, tonicity agent, pH modifier, and a buffer. In another embodiment, the dexamethasone is a salt of dexamethasone. In still another embodiment, the dexamethasone is dexamethasone sodium phosphate.

In one embodiment, the method further comprises sterilizing the fine emulsion to generate the final emulsion, wherein the final emulsion is suitable for injection into a subject.

In one embodiment, the dissolution in ethanol is performed at a temperature of about 25° C. to 80° C., 40° C. to 75° C., 60° C. to 70° C., or at about 25° C., 35° C., 45° C., 60° C., 65° C., 70° C. or 75° C.

In one embodiment, the high-speed homogenization is performed at a speed of about 2,000 rpm (revolutions per minute) to 25,000 rpm. In another embodiment, the high-speed homogenization is performed at a speed of about 20,000 rpm. In yet another embodiment, the high-speed homogenization is performed at a speed of about 3600 rpm.

In one embodiment, the high-speed homogenization is performed for a time period of about 0.5 min to 1 hour, 1 min to 45 min, or 1 min to 30 min. In another embodiment, the high-speed homogenization is performed for a time period of about 20 to 40 min or for about 30 min.

In one embodiment, the high-speed homogenization is performed at about 10° C. to about 60° C., 20° C. to about 60° C., about 30° C. to about 50° C., or about 35° C. to about 45° C. In another embodiment, the high-speed homogenization is performed at about 25° C., 30° C., 35° C., 40° C., 45° C. or 50° C.

In one embodiment, the high-pressure homogenization is performed at a pressure of about 10,000 psi (pounds per square inch) to 30,000 psi. In another embodiment, the high-pressure homogenization is performed at a pressure of about 20,000 psi.

In one embodiment, the high-pressure homogenization is performed with cooling. In another embodiment, the high-pressure homogenization is performed with cooling which is sufficient to bring the temperature of the emulsion at the outlet of the process to about 0° C. to about 60° C., about 10° C. to about 40° C., about 20° C. to about 30° C., or to about 20° C., 25° C. or 30° C. within the time period.

In one embodiment, the sterilizing the fine emulsion comprises filtering the fine emulsion through a nylon filter. In another embodiment, the nylon filter is a Posidyne® filter. In yet another embodiment, the filter has a pore size of about 0.2 µm (micrometers).

Additional embodiments of the present compositions and methods and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIG. 1A: Example 1, FIG. 1B: Example 2, FIG. 1C: Example 3, FIG. 1D: Example 6.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm. As used herein, the term "about" means ±5%, ±10%, or ±20% of the value being modified.

The term "emulsion" or "emulsion formulation" means a colloidal dispersion of two immiscible liquids in the form of droplets, whose diameter, in general, is between 10 nanometers and 100 microns. An emulsion is denoted by the symbol O/W (oil-in-water) if the continuous phase is an aqueous solution and by W/O (water-in-oil) if the continuous phase is an oil. Other examples of emulsions such as O/W/O (oil-in-water-oil) include oil droplets contained within aqueous droplets dispersed in a continuous oil phase.

"Physically stable" emulsions will meet the criteria under USP <729>, which defines universal limits for (1) mean droplet size not exceeding 500 nm or 0.5 µm and (2) the population of large-diameter fat globules, expressed as the volume-weighted percentage of fat greater than 5 µm (PFAT5) not exceeding 0.05%, at 5° C. or room temperature for a designated storage time period. In addition, physically stable emulsions will have no visible aprepitant crystals upon storage at 5° C. or room temperature for a designated time period. Crystals are considered visible when viewed at magnification of 4× to 10×. An emulsion is physically stable if it meets the criteria under USP <729> and aprepitant crystals are not visible upon storage at 5° C. or room temperature for a time period equal to or at least 1 week, 2 weeks, 4 weeks, 1 month, 2 months, 6 months, 1 year or 2 years.

"Chemically stable" emulsions of the disclosure are ones in which the concentration of the active component (i.e., the drug being delivered) does not change by more than about 20% under appropriate storage conditions for at least 1 month. In certain embodiments, the aprepitant concentration in an emulsion of the present disclosure does not change by more than about 5%, 10%, 15% or 20% under appropriate storage conditions for at least 1, 2, 3, 4, 5, 6, 9, 12, 15, 18, or 24 months.

In one example, the stable emulsion compositions of the disclosure are stable over a wide range of temperatures, e.g., −20° C. to 40° C. The compositions of the disclosure may be stored at about 5° C. to about 25° C.

"Oil phase" in a water-in-oil emulsion refers to all components in the formulation that individually exceed their solubility limit in the water phase; these are materials that generally have solubilities of less than 1% in distilled water, however, water phase components such as salts may decrease the solubility of certain oils resulting in their partitioning into the oil phase. The oil phase refers to the non-aqueous portion of a water-in-oil emulsion.

"Aqueous phase" or "water phase" in a water-in-oil emulsion refers to the water present and any components that are water soluble, i.e., have not exceeded their solubility limit in water. "Aqueous phase", as used herein, includes a water-containing liquid which can contain pharmaceutically acceptable additives such as acidifying, alkalizing, buffering, chelating, complexing and solubilizing agents, antioxidants and antimicrobial preservatives, humectants, suspending and/or viscosity modifying agents, tonicity and wetting or other biocompatible materials. The aqueous phase refers to the non-oil portion of a water-in-oil emulsion.

An "emulsifier" refers to a compound that deters the separation of the injectable emulsion into individual oil and aqueous phases. Emulsifiers useful in the present disclosure generally are (1) compatible with the other ingredients of the stable emulsions of the present disclosure, (2) do not interfere with the stability or efficacy of the drugs contained in the emulsions, (3) are stable and do not deteriorate in the preparation, and (4) are non-toxic.

Suitable emulsifiers include, but are not limited to, propylene glycol mono- and di-fatty acid esters, polyoxyethylene sorbitan fatty acid esters, polyoxyethylene fatty acid esters, polyoxyethylene-polyoxypropylene co-polymers and block co-polymers, salts of fatty alcohol sulphates, sorbitan fatty acid esters, esters of polyethylene-glycol glycerol ethers, oil and wax based emulsifiers, glycerol monostearate, glycerine sorbitan fatty acid esters and phospholipids.

A "phospholipid" refers to a triester of glycerol with two fatty acids and one phosphate ion. Exemplary phospholipids useful in the present invention include, but are not limited to, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. The phospholipids can have any combination of fatty acid as its fatty acyl side chain, for example, the phospholipids can have a saturated fatty acid such as a decanoic acid, lauric acid, myristic acid, palmitic acid, stearic acid, icosanoic acid, (a C20 saturated fatty acid); sodium behenic acid, or an unsaturated fatty acid such as myristoleic acid, palmitoleic acid, oleic acid, sodium linoleic acid, alpha linolenic acid, sodium arachidonic acid, eicosapentanoic acid, and the like. The two fatty acyl residues on the phospholipids may be the same or they may be different fatty acids. The phospholipid component of the drug delivery composition can be either a single phospholipid or a mixture of several phospholipids. The phospholipids should be acceptable for the chosen route of administration.

In one aspect, the phospholipids used as emulsifiers in the present invention are naturally occurring phospholipids from a natural origin. For example, naturally occurring lecithin is a mixture of the diglycerides of stearic, palmitic, and oleic acids, linked to the choline ester of phosphoric acid, commonly called phosphatidylcholine, and can be obtained from a variety of sources such as eggs and soya beans. Soy lecithin and egg lecithin (including hydrogenated versions of these compounds) have been characterized in various compositions and are generally recognized to be safe, have combined emulsification and solubilization properties, and tend to be broken down into innocuous substances more rapidly than most synthetic surfactants.

The term "lecithin" includes a complex mixture of acetone-insoluble phosphatides, of which phosphatidylcholine is a significant component. The term lecithin is also used as a synonym for phosphatidylcholine. Useful lecithins include, but are not limited to, eggyolk-, egg-, soybean-, and corn-derived lecithin. In one embodiment, the emulsifier is lecithin, such as egg yolk-derived lecithin. The terms egg lecithin and egg yolk derived lecithin are used interchangeable throughout. The compositions described herein preferably comprise lecithin as an emulsifier.

The amount of phospholipids, by weight, in the emulsions of the present disclosure may be within a range of about 10 wt/wt % to about 20 wt/wt %, 11 wt/wt % to 19 wt/wt %, 11 wt/wt % to 15 wt/wt %, 12 wt/wt % to 13 wt/wt %, 13 wt/wt % to 14 wt/wt %, 13 wt/wt % to 20 wt/wt %, or 12 wt/wt % to 18 wt/wt %. In certain embodiments, the phospholipids in the emulsions are at a concentration, by weight, about 11 wt/wt %, 12 wt/wt %, 12.5 wt/wt %, 13 wt/wt %, 13.5 wt/wt %, 14 wt/wt %, 14.5 wt/wt %, or 15 wt/wt %.

"Oil" refers to an organic liquid of mineral, vegetable, animal, essential or synthetic origin, including, for example, aliphatic or wax-based hydrocarbons, aromatic hydrocarbons or mixed aliphatic and aromatic hydrocarbons.

The term "buffer" or "buffered" as used herein means a solution containing both a weak acid and its conjugate base, whose pH changes only slightly upon addition of acid or base. As used herein, the phrase "buffering agent" means a species whose inclusion in a solution provides a buffered solution.

The term "therapeutic agent" describes any natural or synthetic compound which has a biological activity.

II. Aprepitant Emulsion and Methods of Making

The present disclosure is directed to stable pharmaceutical compositions including aprepitant, a surfactant or mixtures of surfactants, a co-surfactant, an oil, with an aqueous phase. The composition is in the form of an oil-in-water emulsion which remains stable over an extended period of time and which is suitable for dilution and intravenous administration.

The active agent, e.g., aprepitant, is present in the oil phase with an emulsifier, a co-emulsifier and an oil. The oil phase is then combined with an aqueous phase comprising water and a tonicity agent as described below to generate the stable emulsion. Prior to combining the oil phase with the aqueous phase, the oil phase will have an oil:aprepitant ratio of about 13:1. Use of this ratio was surprisingly found to produce, when mixed with the water phase, an emulsion which is more stable as compared to an emulsion in which the oil phase contains an oil:aprepitant ratio of less than about 12:1 or 11:1, and/or greater than about 15:1, 20:1, or 30:1.

Moreover, the present compositions also possess favorable stability properties when the amount of emulsifier in the oil phase is greater than the amount of oil. For example, the oil phase contains an emulsifier:oil ratio of about 5:1 to 1:1, 3:1 to 1:1 or a ratio of about 1.5:1. Such ratios of emulsifier: oil have surprisingly been found to impart greater stability on the final emulsion which is suitable for injection into a patient. For example, an aprepitant emulsion having a phospholipid:oil ratio within the oil phase of about 1.5:1 was found to have greater stability than a similar aprepitant emulsion, wherein the oil phase comprises a phospholipid: oil ratio of about 0.01:1, 0.1:1, 0.5:1 or 0.9:1.

1. Oil Phase

The oil (hydrophobic) phase comprises an oil. Triglycerides are exemplary oils for use in the compositions described herein. In certain embodiments the oil is or comprises a vegetable oil. "Vegetable oil" refers to oil derived from plant seeds or nuts. Vegetable oils are typically "long-chain triglycerides" (LCTs), formed when three fatty acids (usually 14 to 22 carbons in length, with unsaturated bonds in varying numbers and locations, depending on the source of the oil) form ester bonds with the three hydroxyl groups on glycerol. In certain embodiments, vegetable oils of highly purified grade (also called "super refined") are used to ensure safety and stability of the oil-in-water emulsions. In certain embodiments hydrogenated vegetable oils, which are produced by controlled hydrogenation of the vegetable oil, may be used. Exemplary vegetable oils include but are not limited to almond oil, babassu oil, black currant seed oil, borage oil, canola oil, castor oil, coconut oil, corn oil, cottonseed oil, olive oil, peanut oil, palm oil, palm kernel oil, rapeseed oil, safflower oil, soybean oil, sunflower oil and sesame oil. Hydrogenated and/or or partially hydrogenated forms of these oils may also be used. In specific embodiments, the oil is or comprises safflower oil, sesame oil, corn oil, olive oil and/or soybean oil. In more specific embodiments, the oil is or comprises safflower oil, and/or soybean oil. The oil is present in the emulsion at about 9 wt/wt %, though this may vary between about 5 wt/wt % to 12 wt/wt % or 9 wt/wt % to 10 wt/wt %.

The aprepitant is first mixed with an emulsifier such as a phospholipid emulsifier. Examples 1, 2, 3 and 6 below describe emulsions made using an egg lecithin. The phophopholipid emulsifier is added to a concentration of greater than 10 wt/wt %, 11 wt/wt %, 12 wt/wt % or 13 wt/wt % of the emulsion but less than 15 wt/wt %, 17 wt/wt % or 20 wt/wt % of the emulsion.

The mixture of aprepitant and emulsifier is dissolved in a co-emulsifier such as a short chain alcohol (1 to 6 carbons). In Examples 1, 2, 3 and 6 below, the co-emulsifier is ethanol. The mixture is mixed at an elevated temperature, such as at about 60° C. or 70° C. or at an elevated temperature within the range of about 50° C. or 70° C., until the aprepitant and emulsifier are dissolved. This mixture is then combined with the oil, such as soybean oil, by mixing again at an elevated temperature such as at about 60° C. to produce the oil phase containing the aprepitant. Excess co-emulsifier can be removed by standard evaporation methods including heating, or pressure reduction, or a combination thereof such employed in a rotary evaporator. In this process, about 10% to 100%, 20% to 95%, 80% to 100%, 90% to 100%, or 95% to 100% of the ethanol evaporates depending on preparation scale, any pressure reduction, and heating time.

In one embodiment, the aprepitant and the emulsifier are dissolved in a co-emulsifier and an oil. In Examples 1, 2, 3 and 6 below, the co-emulsifier is ethanol, the oil is soybean oil, however, the methods can be used with any one or more of the co-emulsifiers and oils described herein. The mixture is mixed at an elevated temperature, such as at about 60° C. or 70° C. or at an elevated temperature within the range of about 50° C. or 70° C., at least until the aprepitant and emulsifier are dissolved to produce the oil phase containing aprepitant. The mixture of aprepitant, emulsifier, co-emulsifier and oil are mixed at the elevated temperature for about 15 min to 120 min, about 15 min to 45 min, about 30 min to 90 min, or for about 15 min, 30 min or 50 min.

Excess co-emulsifier can be removed by standard evaporation methods including heating, or pressure reduction, or a combination thereof in a rotary evaporator. During this process, about 10% to 100%, 20% to 95%, 80% to 100%, 90% to 100%, or 95% to 100% of the ethanol evaporates depending on preparation scale, any pressure reduction, and heating time.

In one embodiment, dexamethasone is added to the oil phase comprising the aprepitant, emulsifier and oil to generate an oil phase comprising both aprepitant and dexamethasone prior to mixing with the aqueous phase to generate the pharmaceutical emulsion for injection. Dexamethasone is added to the oil phase to provide a dose of about 12 mg dexamethasone.

2. Aqueous Phase

The aqueous phase of the aprepitant emulsion can be a mixture of water and a tonicity agent, including those such as but not limited to sucrose, mannitol, glycerin or dextrose or a mixture thereof. Also included in the aqueous phase is a pH-modifying agent. Sodium oleate is used in Examples 1, 2 and 3 below to adjust the pH of the emulsion to about 6 to 9, depending on the desired emulsion formulation. The aqueous phase is produced by mixing water with the tonicity agent and sodium oleate as the pH modifying agent. Other pH modifiers that may be used include but are not limited to sodium hydroxide, potassium hydroxide, magnesium hydroxide, Tris, sodium carbonate and sodium linoleate. The pH modifier used is effective for adjusting the pH of the emulsion to a preferred pH of about 6 to 9, 7 to 8, or about 6, 7, 8 or 9. The aqueous phase can readily form by mixing at room temperature.

The aqueous phase may further contain a buffering agent to promote stability of the emulsion formulation. The drug substance may degrade; for example, lipophilic drugs will partition into the oil phase, which will confer some degree of protection, but hydrolytic degradation may still occur at the oil-water interface. Possible chemical degradation within parenteral fat emulsions includes oxidation of unsaturated fatty acid residues present in triglyceride and lecithin, and hydrolysis of phospholipids leading to the formation of free fatty acids (FFA) and lysophospholipids. Such degradants lower pH, which may then promote further degradation. Thus, pH should be controlled during manufacture and emulsion formulations may include a buffering agent to provide additional control. Any decrease in pH over the assigned shelf-life may be indicative of chemical degradation. Suitable buffers are well known to the person skilled in the art and include but are not limited to a phosphate buffer, citrate buffer, Tris buffer, carbonate buffer, succinate buffer, maleate buffer or borate buffer. Tris buffer is used in Example 11 below to adjust the pH of the emulsion to about 8 to 9. In a particular embodiment, the buffer is selected from the group, phosphate buffered saline (PBS), modified PBS (PBS-mod) and citrate buffer. In a particular embodiment, the aqueous phase comprises a buffer, that when mixed with the oil phase will provide a substantially isotonic oil in water emulsion.

Buffering agents useful for the presently described compositions include, but are not limited to, a phosphate buffer, citrate buffer, Tris buffer, carbonate buffer, succinate buffer, maleate buffer or borate buffer. In a particular embodiment, the buffer is selected from the group, phosphate buffered saline (PBS), modified PBS (PBS-mod) and citrate buffer. In a particular embodiment, the aqueous phase comprises a buffer, that when mixed with the oil phase will provide a substantially isotonic oil in water emulsion. In some embodiments, when the aqueous phase contains a buffering agent, the aqueous phase does not include a tonicity agent. Also, when a buffer is added to the aqueous phase, a pH-adjusting agent may not be added to the aqueous phase. It is understood that a buffer can be added to the aqueous phase or the buffer can be added to the emulsion.

In some embodiments, the aqueous phase contains a tonicity agent such as sucrose. The tonicity agent is added to an aqueous phase having about 0% to 30%, 0% to 25% or about 20% of the tonicity agent (wt/wt). It was surprisingly found that a composition containing about 20% sucrose wt/wt in the aqueous phase produced an emulsion that was particularly stable as determined by freeze-thaw testing. Accordingly, preferred embodiments include an emulsion in which the aqueous phase comprises a tonicity agent which imparts greater chemical and/or physical stability as compared to an emulsion wherein the aqueous phase contains less than about 10%, 15% or 20% wt/wt tonicity agent or more than about 30%, 40% or 50% wt/wt tonicity agent.

In one embodiment, the aqueous phase further comprises dexamethasone sodium phosphate (also referred to as "dexamethasone phosphate"). Dexamethasone sodium phosphate is a corticosteroid which is freely soluble in water. Daily dosages for dexamethasone sodium phosphate range from about 0.5 mg to 20 mg, more preferably from about 14 mg to 18 mg or 16 mg, depending on the severity of the disease or disorder. Accordingly, an aprepitant emulsion further comprising dexamethasone may contain dexamethasone sodium phosphate in the aqueous phase. Accordingly, the aqueous phase of an emulsion suitable for intravenous administration may contain about 0.5 mg to 20 mg, 14 mg to 18 mg or about 16 mg dexamethasone sodium phosphate.

In another embodiment, a solution of dexamethasone sodium phosphate can be mixed into the fine emulsion prior to sterile filtration to prepare an emulsion containing dexamethasone sodium phosphate in the aqueous phase, 3. Aprepitant Emulsion The pharmaceutical aprepitant compositions of the present disclosure are sterile oil-in-water emulsions comprising the aqueous and oil phases described above. Also encompassed by the disclosure are methods for preparing stable emulsions comprising aprepitant which are suitable for intravenous administration and which can be prepared according to the conventional manufacturing procedures using aseptic techniques.

The aqueous phase is combined with the oil phase, under high-speed homogenization to produce a coarse emulsion. As described in Examples 1, 2, 3, 4, 5 and 6, the combined aqueous and oil phases is homogenized using an IKA Ultra-Turrax T25 dispersing instrument at a speed of 20,000 rpm for 1 min. The speed used in this first homogenization step may vary, for example, from 2000 rpm to 25,000 rpm, or from 15,000 rpm to 22,000 rpm. The time of the homogenization step can also vary, for example, from 0.5 min to 1 hour, or from 1 min to 45 min. This crude emulsion is then homogenized into a fine emulsion by a high-pressure homogenizer, which may be a microfluidizer. The interaction chamber and the cooling coil portions of the microfluidizer are cooled by water, such as by an ice bath. The temperature of the ice bath may be between 0 to 10° C., or 2 to 6° C. The temperature of the emulsion coming out of the high-pressure homogenization may be between 0 to 60° C., 15° C., to 60° C, 20° C. to 40° C., or at about 25° C. The microfluidizer is first primed with water, then the crude emulsion is introduced. The output from the homogenizer is initially run to waste to remove priming water, and priming water and emulsion mixtures, and then collected in a clean vessel when the stream becomes consistent in appearance. The high-pressure homogenizer cycle may be repeated to sufficiently reduce oil droplet size. The pressure used for the homogenization may vary. The pressures may be between 5000 and 30,000 psi. The number of passes through the microfluidizer may vary in order to achieve the desired droplet size. The number of passes may be from about 2 to 20, 2 to 15, 4 to 15, 4 to 12 or 7 to 8.

The pharmaceutical formulation may then be passed through a filter system at room temperature, and/or autoclaved, to achieve sterilization. The filters used to achieve sterilization may be chosen by the skilled artisan and may have a nominal pore size of 0.2 μm. The filter material used may vary. In one embodiment, the filter is nylon. In another embodiment, the filter is a Posidyne® filter (covalent charge-modified Nylon 6,6 membrane which exhibits a net positively-charged zeta potential in aqueous solutions). For large scale production the method above may need to be modified. A skilled practitioner could combine these materials in a different order and using different processing equipment to achieve the desired end result.

In one embodiment of the disclosure, the homogenization can be done in repeated cycles to achieve an emulsion in which the oil particle/globule size is less than 2 microns (μm) with intermediate cooling of the homogenized product to a temperature less than about 25° C.

The final emulsion comprises an oil portion (oil phase) dispersed in an aqueous portion (aqueous phase). The ratio of components to the aprepitant within the oil phase is an important characteristic of the emulsion which may affect stability of the formulation prepared for injection. As described above, the oil phase comprises aprepitant, an oil and an emulsifier, examples of which are provided herein.

The final aprepitant emulsion contains 0.7 wt/wt % aprepitant, but may range from about 0.2 wt/wt % to 1.5 wt/wt %, 0.4 wt/wt % to 1.0 wt/wt % or 0.6 wt/wt % to 0.7 wt/wt %. An emulsion is prepared which contains about 130 mg aprepitant, however, preparations may also be prepared according to the present disclosure which contain about 100 mg to 1000 mg, 100 mg to 500 mg, 250 mg to 750 mg or 100 mg to 200 mg aprepitant.

In one embodiment, the ratio of oil:aprepitant (wt %:wt %) within the oil phase ranges from about 11:1 to 15:1, 12:1 to 14:1, 13:1 to 13.5:1, 13:1 to 14:1, or 12:1 to 15:1. In another embodiment, the ratio of oil: aprepitant is about 11:1, 11.5:1, 12:1, 12.5:1, 13:1, 13.5:1, 14:1, 14.5:1 or 15:1.

The ratio of emulsifier to aprepitant may also vary. For example, the ratio of emulsifier:aprepitant (wt %:wt %) within the oil portion ranges from about 15:1 to 30:1, 20:1 to 25:1, 18:1 to 22:1 or 10:1 to 30:1. In one embodiment, the emulsifier:aprepitant (wt %:wt %) is about 15:1, 18:1, 19:1, 20:1, 21:1, 22:1 or 23:1.

The ratio of components within the oil phase may alternatively be expressed in the ratio of (emulsifier plus oil):aprepitant (wt %:wt %). Ratios envisioned in the present disclosure may range from about 20:1 to 40:1, 25:1 to 35:1, 30:1 to 35:1 or 33:1 to 37:1, or may be, for example, about 30:1, 32:1, 33:1, 34:1, 35:1, 36:1, 37:1, 38:1 or 40:1.

The composition of the present disclosure has a significant advantage in terms of reduced toxicity as compared to injectable formulations which may contain less desirable excipients such as detergents, e.g., Tween-20 or Tween-80. The present formulations take advantage of the ability to solubilize therapeutically effective amounts of aprepitant in an oil phase which can then be used to generate an emulsion suitable for injection. Accordingly, described herein are pharmaceutical emulsion compositions containing aprepitant and optionally dexamethasone or dexamethasone sodium phosphate, wherein the emulsion does not comprise a detergent.

The composition of the present disclosure gives a product suitable for parenteral use because of low particle size. The composition of the present disclosure is easy to use as the product can be diluted with an agent such as an aqueous solution of sucrose, an aqueous solution of maltose or dextrose 5% injection or normal saline to achieve the required concentration for parenteral administration. The composition of the present disclosure also has a prolonged shelf life and hence is suitable for a readily marketable product.

The compositions of the disclosure are both chemically and physically stable. A physically stable emulsion of the invention is one which can be stored under appropriate conditions for at least 1, 2, 3, 4, 5, 6, 9, 12, 15, 18, 24 or 36 months, without an increase in average droplet size above that allowed as stated in USP <729>. As well, the population of large-diameter fat globules should be within the limits stated in USP <729>.

Droplet size limits defined in USP <729> apply throughout the assigned shelf life, which for a commercial pharmaceutical formulation may extend to 2-3 years or longer. All true emulsions are thermodynamically unstable and may over time undergo a range of processes which tend to increase the droplet size. These include direct droplet coalescence, when two droplets collide and form a single new droplet, and aggregation, in which droplets adhere together to form larger masses. Aggregation may in some cases be a precursor of further coalescence into larger droplets. These processes may result in large aggregates rising to the surface of the container, a phenomenon known as 'creaming', and ultimately to free oil being visible on the emulsion surface, known as 'cracking'.

Droplet size measurements such as those defined in USP<729> can measure the initial increases in size, and hence are predictive of emulsion physical stability, at early times, long before the formulation shows macroscopic visible changes. Accordingly, the emulsions as described herein are stable compositions having an intensity-weighted mean droplet diameter less than about 500 nm, 400 nm, 300 nm, 200 nm or 100 nm.

The oil or particle droplet size, i.e. diameter, according to the present disclosure is measured using a dynamic light scattering (DLS) instrument, such as the Malvern Zetasizer 4000, Malvern Zetasize Nano S90 or preferably the Malvern Zetasizer Nano ZS. Intensity-weighted particles sizes were recorded, since they do not require the knowledge of the refractive index of the particle. In Malvern Zetasizer instruments, there are two fits for determining the intensity-weighted diameter of the oil droplet size. The first is a cumulant fit that is used to determine the Z-average diameter; this fit can additionally give the polydispersity index (PDI). This cumulant fit is recommended for monodisperse samples possessing a PDI of lower than 0.2. The second is a non-negative least squares (NNLS) fit. This gives the Peak 1 diameter, Peak 2 diameter and Peak 3 diameter. This is more suitable for polydisperse samples having a PDI of greater than 0.2.

The emulsion preparations as described herein may further comprise a preservative in quantities that preserve the composition. Suitable preservatives used in some of the embodiments of present disclosure include, but are not limited to, disodium edetate, tocopherol, benzalkonium chloride, methyl, ethyl, propyl or butylparaben, benzyl alcohol, phenylethyl alcohol, benzethonium, chlorobutanol, potassium sorbate or combination thereof.

III. Medical Use

The pharmaceutical compositions of the present disclosure can be used for the prevention or treatment of emesis and provide a non-oral option for patients undergoing highly or moderately emetogenic chemotherapy. The disclosure thus encompasses a method of treatment comprising intravenously administering an aprepitant emulsion as described herein to a subject undergoing highly or moderately emetogenic chemotherapy.

Another embodiment relates to the use of the pharmaceutical formulations of the disclosure in the manufacture of a medicament for use preventing or treating emesis in a subject in need thereof.

The amount of the aprepitant and optionally dexamethasone required for use in the methods of the disclosure may vary with the method of administration and condition of the patient, and the degree of therapy required, and will be ultimately at the discretion of the attendant physician or clinician.

IV. EXAMPLES

The following examples are illustrative in nature and are in no way intended to be limiting.

Preparation of Aprepitant Emulsions for Intravenous Injection

Example 1

Figure 1A:
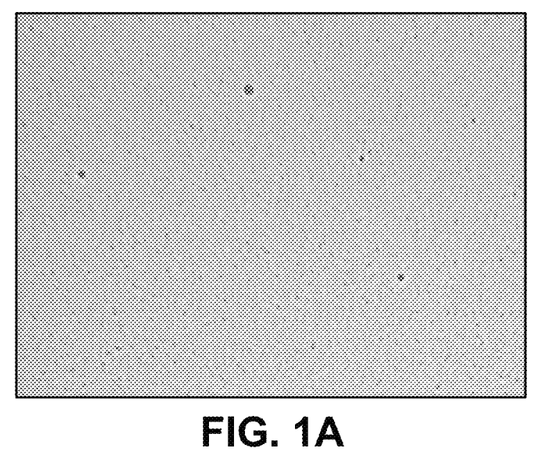
FIGS. 1A-1D provides microscope images of samples from Examples 1, 2, 3 and 6 after a freeze-thaw cycle.

To prepare the aprepitant emulsion, an oil phase was first prepared by combining 750 mg of aprepitant and 15.0 g of egg lecithin (LIPOID E 80) with 12.0 ml of ethanol. This mixture was dissolved by heating and stirring at 60° C. and 200 rpm for 15 min. To the resultant solution was added in 10.0 g of soybean oil. Heating at 60° C. and stirring at 200 rpm was continued for another 15 min. The aqueous phase was prepared by dissolving 5.60 g of sucrose and 0.500 g of sodium oleate in 70.0 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 μm nylon syringe filter (Corning). The details of the emulsion composition are provided in Table 1 below and a microscope image of the sample is provided in FIG. 1A. By dynamic light scattering (Malvern® Zetasizer Nano ZS), the intensity-weighted particle size analyzed using non-negative least squares (NNLS) fit gave a Peak 1 diameter of 99 nm. The intensity-weighted mean particle size determined using cumulant fit provided a Z-average diameter of 87 nm. The zeta potential was measured to be −43 mV by laser Doppler micro-electrophoresis (Malvern® Zetasizer Nano ZS). The pH of the injectable emulsion was 8.74. This aprepitant-containing emulsion can be injected as is, or diluted for infusion with 5% dextrose or 0.9% saline.

TABLE 1

| Component | Amount (g) | Concentration (w/w %) | Ratio to Aprepitant |
|---|---|---|---|
| Aprepitant | 0.750 | 0.679 | 1 |
| Lipoid E 80 | 15.0 | 13.6 | 20 |
| Soybean Oil | 10.0 | 9.05 | 13.3 |
| Ethanol[1] | 8.59 | 7.78 | 11.5 |
| Sucrose | 5.60 | 5.07 | 7.5 |
| Sodium Oleate | 0.500 | 0.453 | 0.667 |
| Water for Injection | 70.0 | 63.4 | 93.3 |
| Total | 110 | 100 | — |

[1]Final amount after taking into account the ethanol that was evaporated during processing.

Example 2

Figure 1B:
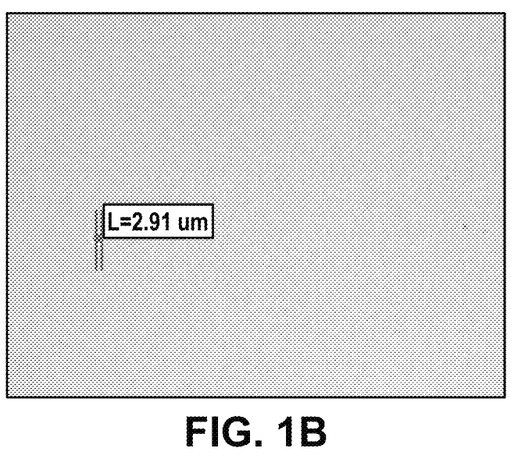

To prepare the aprepitant emulsion, an oil phase was first prepared by combining 450 mg of aprepitant and 9.00 g of egg lecithin (LIPOID E 80) with 4.0 ml of ethanol. This mixture was dissolved by heating and stirring at 60° C. and 200 rpm for 15 min. To the resultant solution was added 6.00 g of soybean oil. Heating at 60° C. and stirring at 200 rpm was continued for another 15 min. The aqueous phase was prepared by dissolving 3.36 g of sucrose and 0.300 g of sodium oleate in 42.0 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 μm nylon syringe filter (Corning). The details of the emulsion composition are provided in Table 2 below and a microscope image of the sample is provided in FIG. 1B. By dynamic light scattering (Malvern® Zetasizer Nano ZS), the intensity-weighted particle size analyzed using NNLS fit gave a Peak 1 diameter of 127 nm. The intensity-weighted mean particle sized determined using cumulant fit provided a Z-average diameter of 101 nm. The zeta potential was measured to be −47 mV by laser Doppler micro-electrophoresis (Malvern® Zetasizer Nano ZS). The pH of the injectable emulsion was 8.77. This aprepitant-containing emulsion can be injected as is, or diluted for infusion with 5% dextrose or 0.9% saline.

TABLE 2

| Component | Amount (g) | Concentration (w/w %) | Ratio to Aprepitant |
|---|---|---|---|
| Aprepitant | 0.450 | 0.714 | 1 |
| Lipoid E 80 | 9.00 | 14.3 | 20 |
| Soybean Oil | 6.00 | 9.52 | 13.3 |
| Ethanol[1] | 1.89 | 3.00 | 4.20 |
| Sucrose | 3.36 | 5.33 | 7.47 |
| Sodium Oleate | 0.300 | 0.476 | 0.667 |
| Water for Injection | 42.0 | 66.7 | 93.3 |
| Total | 63.0 | 100 | — |

[1]Final amount after taking into account the ethanol that was evaporated during processing.

Example 3

To prepare the aprepitant emulsion, an oil phase was first prepared by combining 450 mg of aprepitant and 9.00 g of egg lecithin (LIPOID E 80) with 6.0 ml of ethanol. This mixture was dissolved by heating and stirring at 60° C. and 200 rpm for 15 min. To the resultant solution was added in 6.00 g of soybean oil. Heating at 60° C. and stirring at 200 rpm was continued for another 15 min. The aqueous phase was prepared by dissolving 15.62 g of sucrose and 0.300 g of sodium oleate in 42.0 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 μm nylon syringe filter (Corning). The details of the emulsion composition are provided in Table 3 below and a microscope image of the sample is provided in FIG. 1C. By dynamic light scattering (Malvern® Zetasizer Nano ZS), the intensity-weighted particle size analyzed using NNLS fit gave a Peak 1 diameter of 88 nm. The intensity-weighted mean particle sized determined using cumulant fit provided a Z-average diameter of 68 nm. The zeta potential was measured to be −42 mV by laser Doppler micro-electrophoresis (Malvern® Zetasizer Nano ZS). The pH of the injectable emulsion was 8.80. This aprepitant-containing emulsion is to be diluted with water for injection by 4-fold prior to injection.

TABLE 3

| Component | Amount (g) | Concentration (w/w %) | Ratio to Aprepitant |
|---|---|---|---|
| Aprepitant | 0.450 | 0.587 | 1 |
| Lipoid E 80 | 9.00 | 11.7 | 20 |
| Soybean Oil | 6.00 | 7.83 | 13.3 |
| Ethanol[1] | 3.27 | 4.26 | 7.26 |
| Sucrose | 15.6 | 20.4 | 34.7 |
| Sodium Oleate | 0.300 | 0.391 | 0.667 |
| Water for Injection | 42.0 | 54.8 | 93.3 |
| Total | 76.6 | 100 | — |

[1]Final amount after taking into account the ethanol that was evaporated during processing.

Example 4

Alternate Aprepitant Emulsion Formulation for Intravenous Injection

An aprepitant emulsion was prepared which has less than 10% wt/wt of the phospholipid emulsifier and which was adjusted to a pH of less than 8.0. To prepare the aprepitant emulsion, an oil phase was first prepared by combining 450 mg of aprepitant and 6.67 g of egg lecithin (LIPOID E 80) with 7.2 ml of ethanol. This mixture was dissolved by heating and stirring at 60° C. and 200 rpm. Heating and stirring was carried out until the ethanol was evaporated and a thick residue was observed. To the resultant solution was added in 6.00 g of soybean oil and an appropriate amount of ethanol to obtain a clear oil phase upon heating at 60° C. The aqueous phase was prepared by dissolving 3.36 g of sucrose in 50.5 ml of water for injection at 60° C. The aqueous phase was then added to the oil phase and subsequently subjected to high-speed homogenization (Ultra-Turrax® IKA T25) at a speed of 20,000 rpm for 1 min to produce the crude emulsion. The pH of this crude emulsion was adjusted to 7.0 and then passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 μm nylon syringe filter (Corning). The details of the emulsion composition are provided in Table 4 below. Within 4 days post preparation at room temperature, crystals were observed in the product by microscopy.

TABLE 4

| Component | Amount (g) | Concentration (w/w %) | Ratio to Aprepitant |
|---|---|---|---|
| Aprepitant | 0.450 | 0.672 | 1 |
| Lipoid E 80 | 6.67 | 9.95 | 14.8 |
| Soybean Oil | 6.00 | 8.96 | 13.3 |
| Sucrose | 3.36 | 5.02 | 7.47 |
| Water for Injection | 50.5 | 75.4 | 112 |
| Total | 67.0 | 100 | — |

Example 5

An aprepitant emulsion was prepared which contains oleic acid. To prepare the aprepitant emulsion, an oil phase was first prepared by combining 250 mg of aprepitant, 2.50 g of egg lecithin (LIPOID E 80), 15.0 g of soybean oil and 125 mg of oleic acid. Ten ml of ethanol was added to dissolve the mixture at 70° C. The ethanol was removed by pressure reduction in a 70° C. water bath to yield a clear oil phase. A preheated aqueous phase containing 82.1 ml of water for injection at 70° C. was added to the oil phase and subsequently subjected to high-speed homogenization (Ultra-Turrax® IKA T25) at a speed of 20,000 rpm for 1 min to produce the crude emulsion. This crude emulsion was passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 µm nylon syringe filter (Corning). The details of the emulsion composition are provided in Table 5 below. Within 4 days post-preparation at room temperature, crystals were observed in the product by microscopy.

TABLE 5

| Component | Amount (g) | Concentration (w/w %) | Ratio to aprepitant |
|---|---|---|---|
| Aprepitant | 0.250 | 0.250 | 1 |
| Lipoid E 80 | 2.50 | 2.50 | 10 |
| Soybean Oil | 15.0 | 15.0 | 60 |
| Oleic Acid | 0.125 | 0.125 | 0.5 |
| Water for Injection | 82.1 | 82.1 | 328 |
| Total | 100 | 100 | — |

Example 6

Preparing Emulsions Containing Aprepitant and Dexamethasone Sodium Phosphate for Intravenous Injection To prepare an injectable emulsion containing aprepitant and dexamethasone sodium phosphate, an oil phase was first prepared by combining 773 mg of aprepitant and 15.5 g of egg lecithin (LIPOID E 80) with 10.3 ml of ethanol. This mixture was dissolved by heating and stirring at 60° C. and 200 rpm for 15 min. To the resultant solution was added in 10.3 g of soybean oil. Heating at 60° C. and stirring at 200 rpm was continued for another 15 min. The aqueous phase was prepared by dissolving 5.77 g of sucrose and 0.515 g of sodium oleate in 71.1 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-110L, F12Y interaction chamber) at a pressure of 18,000 psi. Dexamethasone sodium phosphate (93.5 mg) dissolved in 1 ml of water for injection was mixed into the fine emulsion. This resultant fine emulsion containing both aprepitant and dexamethasone sodium phosphate was sterilized by passing it through a 0.2 µm nylon syringe filter (Corning). The details of the emulsion composition are provided in Table 6 below and a microscope image of the sample is provided in FIG. 1D. By dynamic light scattering (Malvern® Zetasizer Nano ZS), the intensity-weighted particle size analyzed using NNLS fit gave a Peak 1 diameter of 95 nm. The intensity-weighted mean particle size determined using cumulant fit provided a Z-average diameter of 70 nm. The zeta potential was measured to be −43 mV by laser Doppler micro-electrophoresis (Malvern® Zetasizer Nano ZS). The pH of the injectable emulsion was 8.92. This aprepitant and dexamethasone sodium phosphate containing emulsion can be injected as is, or diluted for infusion with 5% dextrose or 0.9% saline.

TABLE 6

| Component | Amount (g) | Concentration (w/w %) | Ratio to aprepitant |
|---|---|---|---|
| Aprepitant | 0.773 | 0.688 | 1 |
| Dexamethasone Sodium Phosphate | 0.0935 | 0.0832 | 0.121 |
| Lipoid E 80 | 15.5 | 13.8 | 20 |
| Soybean Oil | 10.3 | 9.17 | 13.3 |
| Ethanol[1] | 7.31 | 6.51 | 9.47 |
| Sucrose | 5.77 | 5.14 | 7.47 |
| Sodium Oleate | 0.515 | 0.459 | 0.667 |
| Water for Injection | 72.1 | 64.2 | 93.3 |
| Total | 112 | 100 | — |

[1]Final amount after taking into account the ethanol that was evaporated during processing.

Example 7

Stability of the Aprepitant Emulsion at Room Temperature and 5° C.

Stability of the aprepitant emulsions prepared as described in Examples 1, 2 3 and 6 was measured by incubating each emulsion preparation at room temperature (about 25° C.) or at 5° C. Mean particle size and percentage of fat globules above 5 µm were measured using DLS and light obscuration respectively to determine if they satisfy USP <729>. The emulsions were also inspected by microscopy for aprepitant crystals. Example 1 was stable at room temperature for 2 months, that is, the mean particle size and percentage of fat globules above 5 µm satisfied USP <729>. Additionally, no aprepitant crystals were visible by microscopy. After 2 months storage at room temperature, creaming was observed in Examples 1 and 6. This corresponded with the observation of aprepitant crystals. Examples 2 and 3 were stable at room temperature for 3 and 2 months respectively. After these time points, aprepitant crystals were observed in these formulations. Storage at 5° C. resulted in longer emulsion stability for Examples 1, 2, 3 and 6. Table 7 shows the characterizations of Examples 1, 2, 3 and 6 and their respective stabilities at room temperature and at 5° C.

TABLE 7

| Sample | PDI | Particle Size as Peak 1 Diameter (nm) | Particle Size as Z-Average Diameter (nm) | Zeta Potential (mV) | pH | Stability at 25° C. per USP <729> (months) | Stability at 5° C. per USP <729> |
|---|---|---|---|---|---|---|---|
| Example 1 | 0.122 | 99 | 87 | −43 | 8.74 | 2 | >10 months |
| Example 2 | 0.200 | 127 | 101 | −47 | 8.77 | 3 | >10 months |
| Example 3 | 0.219 | 88 | 68 | −42 | 8.80 | 2 | >10 months |
| Example 6 | 0.244 | 95 | 70 | −43 | 8.92 | 2 | >10 months |

Example 8

Stability of the Aprepitant Emulsion to Freeze-Thaw Cycle

Figure 1C:
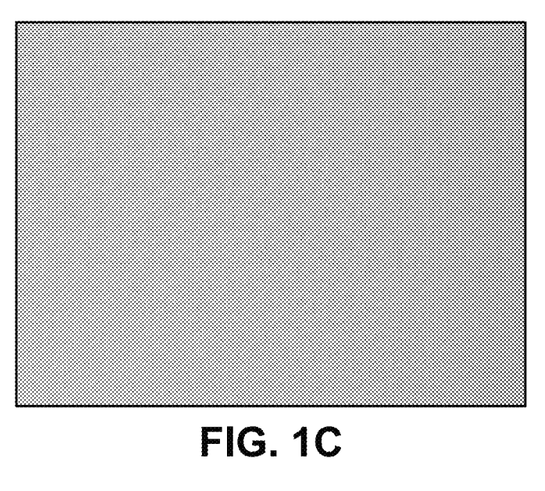
Figure 1D:
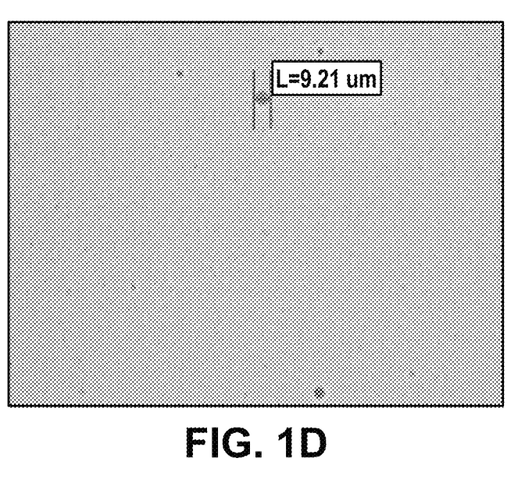

The aprepitant emulsions prepared according to Examples 1, 2, 3 and 6 were tested for stability upon exposure to a freeze-thaw cycle. Samples from the Examples 1, 2, 3 and 6 were stored at −20° C. overnight. They were thawed to room temperature the next day and visualized by microscopy. Prior to freezing, all samples did not present any visible particles under the microscope. FIG. 1 shows microscope images, at 10×, of emulsions after the freeze-thaw cycle (Examples 1, 2, 3 and 6 are shown as FIGS. 1A, B, C, and D, respectively). Emulsions prepared as described in examples 1, 2 and 6 showed visible particles after exposure to freezing. Only Example 3 was stable after freezing. As FIG. 1C shows, no visible particles were observed for the formulation of Example 3. This enhanced stability was conferred by the presence of a large concentration of sucrose (20 w/w % in Example 3 compared to 5 w/wt % in Examples 1, 2 and 6).

Example 9

Figure 2:
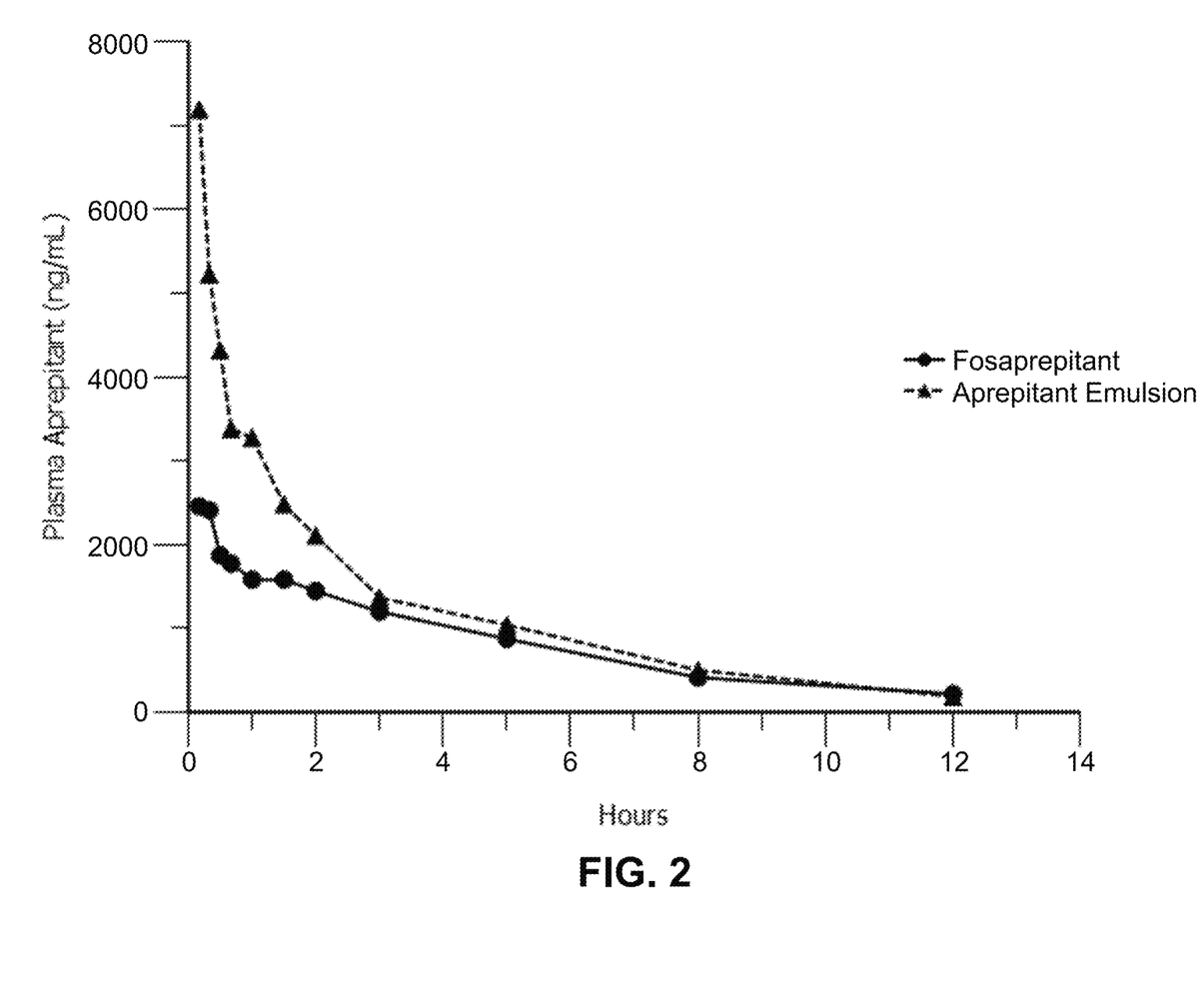
FIG. 2 shows plasma levels of aprepitant after injection of a fosaprepitant solution (●) or an aprepitant emulsion prepared as described herein (▲).

The pharmacokinetics of an aprepitant emulsion prepared according to Example 1 was determined. Two groups of six male Sprague-Dawley rats each were injected intravenously with, respectively, fosaprepitant in solution or aprepitant emulsion prepared according to Example 1. All drugs were administered at an effective concentration equivalent to 14 mg/kg aprepitant. Blood from all rats was collected at the appropriate time intervals and processed to plasma by centrifugation. Plasma samples were analyzed by LC-MS/MS for aprepitant and fosaprepitant, as appropriate. A plasma concentration versus time curve of aprepitant for the emulsion described in Example 1 and for fosaprepitant is presented in FIG. 2 (fosaprepitant in solution, ●; aprepitant emulsion, ▲). The curves indicate the initial aprepitant level reached immediately after injection of the aprepitant emulsion was almost 3 times higher than the initial aprepitant level reached immediately after injection of the fosaprepitant solution. Plasma levels of aprepitant resulting from each injection, however, were essentially the same by the 3-hour time point indicating the formulations were bioequivalent except for a delay in the conversion of fosaprepitant to aprepitant.

Example 10

The pharmacokinetics of an aprepitant and dexamethasone sodium phosphate combination emulsion prepared according to Example 6 was determined. Male Sprague-Dawley rats each were injected intravenously with fosaprepitant solution (group 1), dexamethasone sodium phosphate solution (group 2), or an emulsion containing aprepitant and dexamethasone sodium phosphate prepared according to Example 6 (group 3). Groups 1 and 2 consisted of six rats each; for group 3, twelve rats were injected with the aprepitant and dexamethasone sodium phosphate combination emulsion to allow for the collection of sufficient samples for the measurement of both active ingredients.

In groups 1 and 3, a dose was administered at an effective drug concentration equivalent to 2 mg/kg aprepitant. In groups 2 and 3, a dose was administered at an effective drug concentration equivalent to 0.24 mg/kg dexamethasone sodium phosphate. Blood from all rats was collected at the appropriate time intervals and processed to plasma by centrifugation. Plasma samples were analyzed by LC-MS/MS for dexamethasone, aprepitant, and fosaprepitant, as appropriate.

Figure 3:
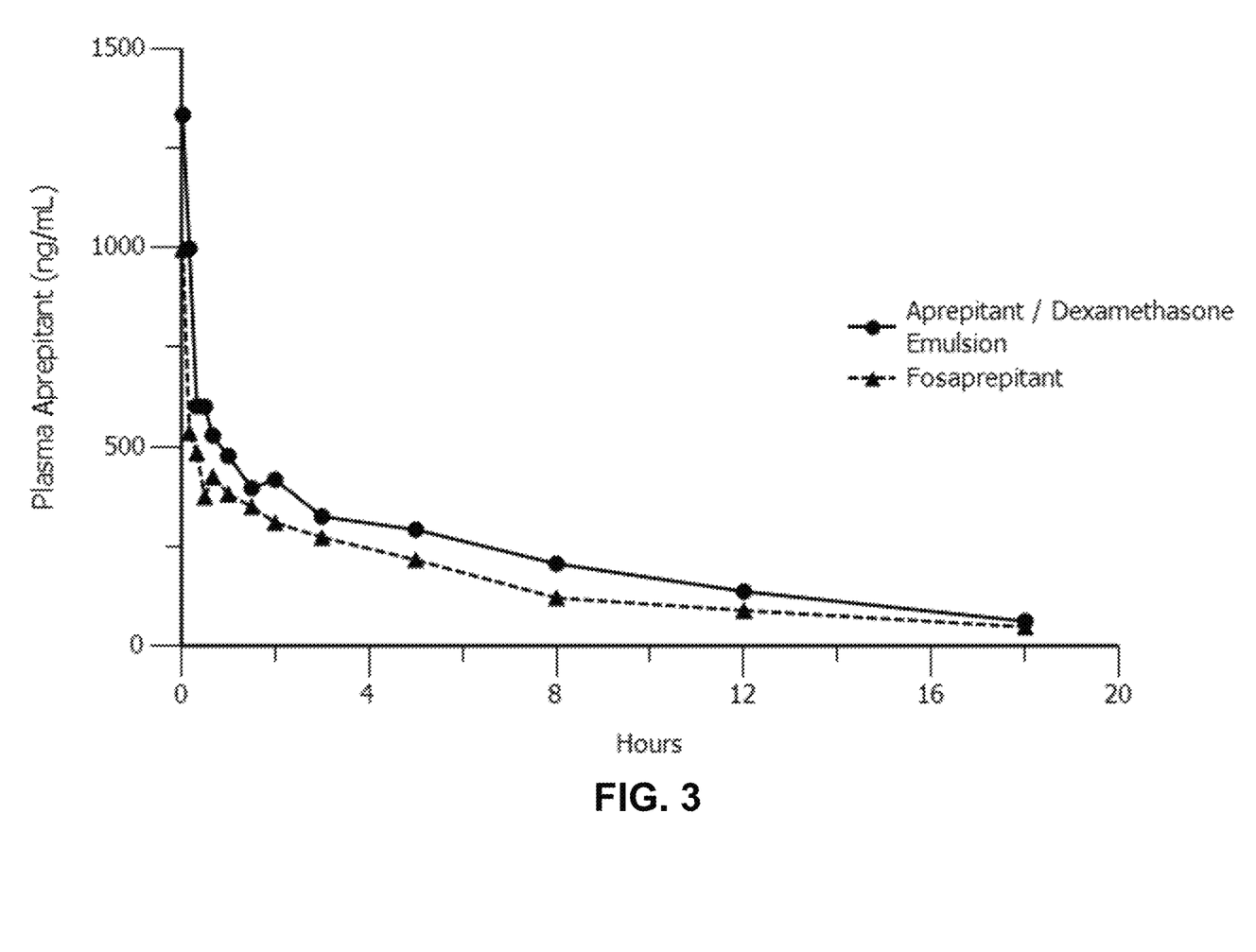
FIG. 3 shows plasma levels of aprepitant after injection of a solution of fosaprepitant (▲) or after injection of an emulsion containing aprepitant and dexamethasone prepared as described herein (●).
Figure 4:
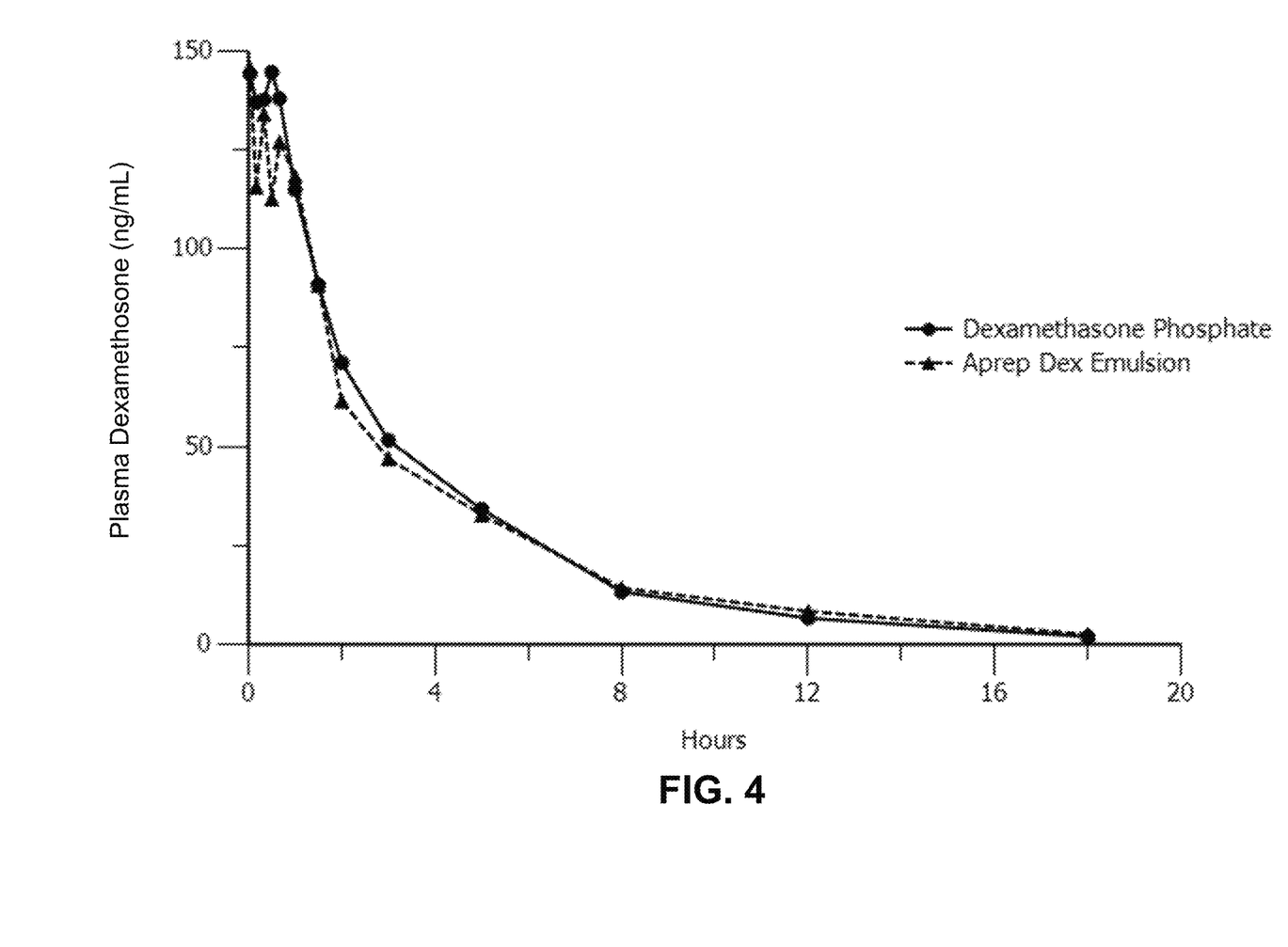
FIG. 4 shows plasma levels of dexamethasone after injection of a solution of dexamethasone sodium phosphate (●) or after injection of an emulsion containing aprepitant and dexamethasone prepared as described herein (▲).

FIGS. 3 and 4 present the plasma concentration versus time curve of aprepitant and dexamethasone, respectively. FIG. 3 compares the aprepitant plasma concentration versus time curve resulting from injection of the emulsion described in Example 6 (FIG. 3, ●) vs. injection of a solution of fosaprepitant (FIG. 3, ▲). FIG. 4 compares the dexamethasone plasma concentration versus time curve resulting from injection of a dexamethasone sodium phosphate solution (FIG. 4, ●) vs. injection of the emulsion described in Example 6. The curves indicate that the aprepitant in the emulsion is released approximately simultaneously with the dexamethasone sodium phosphate. The presence of dexamethasone sodium phosphate in the emulsion does not affect the pharmacokinetics of aprepitant.

Example 11

To prepare the aprepitant emulsion comprising a buffering agent, an oil phase is first prepared by combining 750 mg of aprepitant, 15.0 g of egg lecithin (LIPOID E 80), 10.0 g of soybean oil and 3.75 ml of ethanol. This mixture is dissolved by heating and stirring at 70° C. and 200 rpm for 30 min. The aqueous phase is prepared by dissolving 2.17 g of sucrose and 0.500 g of sodium oleate in a mixture of 4.1 ml of 1M Tris buffer (pH 8.4) and 65.9 ml of water for injection. This mixture is stirred at 300 rpm at room temperature for 30 min. The aqueous phase is then added to the oil phase and subsequently subjected to high-speed homogenization (Ultra-Turrax® IKA T25) at a speed of 20,000 rpm for 1 min to produce the crude emulsion. This crude emulsion is then passed 8 times through an ice-cooled high-pressure microfluidizer (Microfluidizer® M-110L, F12Y interaction chamber) at a pressure of 18,000 psi. The resultant fine emulsion is sterilized by passing it through a 0.2 μm nylon syringe filter (Corning). Dynamic light scattering is used to determine the intensity-weighted particle size using NNLS fit to give the Peak 1 diameter, the intensity-weighted mean particle sized is determined using cumulant fit to provide the Z-average diameter. The zeta potential is measured by laser Doppler micro-electrophoresis (Malvern® Zetasizer Nano ZS). This aprepitant-containing emulsion can be injected as is, or diluted for infusion with 5% dextrose or 0.9% saline.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. An injectable emulsion, comprising:
   aprepitant;
   13 wt/wt % to 20 wt/wt % of an egg lecithin;
   9 wt/wt % to 10 wt/wt % of soybean oil;
   a co-emulsifier which is an alcohol, wherein the alcohol is present in the emulsion at less than 10 wt/wt %;
   a tonicity modifier;
   a pH modifier, wherein the pH modifier is sodium oleate; and
   water;
   wherein the ratio of egg lecithin to aprepitant is between about 20:1 to 25:1;
   wherein the pH of the emulsion ranges from about 7.5 to 9.0; and,
   wherein the emulsion is physically stable.

2. The emulsion of claim 1, wherein the egg lecithin is present in the emulsion at about 16 wt/wt %.

3. The emulsion of claim 1, wherein the egg lecithin is present in the emulsion at about 17 wt/wt %.

4. The emulsion of claim 1, wherein the ratio of egg lecithin to aprepitant is between about 24:1 to 25:1.

5. The emulsion of claim 1, wherein the ratio of egg lecithin to aprepitant is about 24:1.

6. The emulsion of claim 1, wherein the ratio of egg lecithin to aprepitant is about 25:1.

7. The emulsion of claim 1, wherein the alcohol in the emulsion is ethanol.

8. The emulsion of claim 7, wherein the ethanol is present in the emulsion at a concentration of about 2 wt/wt % to 3 wt/wt %.

9. The emulsion of claim 1, wherein the tonicity modifier in the emulsion is sucrose.

10. The emulsion of claim 9, wherein the sucrose is present at a concentration of about 3 wt/wt % to 8 wt/wt %.

11. The emulsion of claim 9, wherein the sucrose is present at a concentration of about 5 wt/wt %.

12. The emulsion of claim 1, wherein the pH modifier in the emulsion is sodium oleate.

13. The emulsion of claim 12, wherein the sodium oleate is present at a concentration of about 0.4 wt/wt % to 0.5 wt/wt %.

14. The emulsion of claim 1, wherein the aprepitant is present in the emulsion at about 0.7 wt/wt %.

15. The emulsion of claim 14, wherein the ratio of egg lecithin to aprepitant is between about 20:1 to 25:1.

16. The emulsion of claim 14, wherein the egg lecithin is present at a concentration of about 16 wt/wt %.

17. The emulsion of claim 14, wherein the egg lecithin is present at a concentration of about 17 wt/wt %.

18. The emulsion of claim 14, wherein the egg lecithin is present at a concentration of about 18 wt/wt %.

19. The emulsion of claim 14, wherein the ratio of egg lecithin to aprepitant is about 24:1.

20. The emulsion of claim 14, wherein the ratio of egg lecithin to aprepitant is about 25:1.

21. The emulsion of claim 1, comprising:
   about 16 wt/wt % to 17 wt/wt % of the egg lecithin;
   about 9 wt/wt % to 10 wt/wt % of the alcohol;
   about 3 wt/wt % to 8 wt/wt % of the tonicity modifier; and
   about 0.4 wt/wt % to 0.5 wt/wt % of the pH modifier.

22. The emulsion of claim 21, wherein the ratio of egg lecithin to aprepitant is between about 24:1 to 25:1.

23. The emulsion of claim 14, comprising:
   about 16 wt/wt % to 17 wt/wt % of the egg lecithin;
   about 9 wt/wt % to 10 wt/wt % of the alcohol;
   about 3 wt/wt % to 8 wt/wt % of the tonicity modifier; and
   about 0.4 wt/wt % to 0.5 wt/wt % of the pH modifier.

24. The emulsion of claim 23, wherein the ratio of egg lecithin to aprepitant is between about 24:1 to 25:1.

* * * * *